United States Patent [19]

Kammann, Jr. et al.

[11] Patent Number: 4,601,838
[45] Date of Patent: Jul. 22, 1986

[54] WATER-SOLUBLE CHLORINATED FATTY ESTER ADDITIVES

[75] Inventors: Karl P. Kammann, Jr., Crown Point, Ind.; Terrence L. Wagner, Crete, Ill.

[73] Assignee: Ferro Corporation, Cleveland, Ohio

[21] Appl. No.: 799,667

[22] Filed: Nov. 19, 1985

[51] Int. Cl.$^4$ .................. C11C 3/00; C10M 173/00
[52] U.S. Cl. ........................... 252/49.3; 252/54.6; 260/408
[58] Field of Search ............... 260/408; 252/49.3, 54.6

[56] References Cited

U.S. PATENT DOCUMENTS

| | | | |
|---|---|---|---|
| 2,812,307 | 11/1957 | Jaives | 252/54.6 |
| 3,080,404 | 7/1963 | Klug et al. | 260/408 |
| 3,492,232 | 1/1970 | Rosenberg | 252/49.3 |
| 3,770,784 | 11/1973 | Clark | 260/408 |
| 3,806,457 | 4/1974 | Brown | 252/54.6 |
| 3,859,318 | 1/1975 | Lesuer | 252/54.6 |
| 3,957,854 | 5/1976 | Miller | 260/408 |
| 4,043,925 | 8/1977 | Felton | 252/49.3 |
| 4,152,915 | 5/1979 | Bussi et al. | 260/408 |
| 4,172,800 | 10/1979 | Walker | 252/49.3 |
| 4,517,100 | 5/1983 | Nance et al. | 252/49.3 |

FOREIGN PATENT DOCUMENTS

| | | | |
|---|---|---|---|
| 2034918 | 3/1971 | Fed. Rep. of Germany | 260/408 |
| 566829 | 7/1977 | U.S.S.R. | 260/408 |

OTHER PUBLICATIONS

Menting et al., "J. of the Am. Chemists Soc.", vol. 46, No. 2, pp. 85–87, reprint.

Primary Examiner—J. E. Evans
Attorney, Agent, or Firm—Philip Hill; Milton L. Simmons

[57] ABSTRACT

Improved additive compositions for use in metalworking fluids comprise nonionic water-soluble chlorinated fatty esters. Improved anti-wear and extreme-pressure performance is realized when employed in synthetic fluids.

10 Claims, No Drawings

WATER-SOLUBLE CHLORINATED FATTY ESTER ADDITIVES

BACKGROUND OF THE INVENTION

The utilization of water-based metalworking lubricants and coolants has become well established in light- to medium-duty applications such as cutting and grinding. Such metalworking fluids include true solutions or "synthetic" fluids, "semi-synthetic" fluids which contain some mineral oil, and emulsions, generally referred to as soluble oils. Such fluids not only remove heat but also serve to inhibit corrosion, lubricate, reduce surface tension, provide extreme-pressure lubrication, and control bacterial growth.

With increasing environmental demands, relating both to use and disposal, emphasis has been placed on the use of synthetic fluids, thus avoiding the presence of mineral oils. Although many advances have been made in providing suitable synthetic fluids, there remains a need for improved anti-wear, lubrication and extreme-pressure performance. This need is especially felt where recent advances in machine tool design require higher feed and cutting speeds as well as higher pressures and temperatures. Improvements in synthetic fluids are also particularly needed in the heavy-duty metal shaping and forming operation such as broaching and drawing.

The older oil-based lubricant additives provided suitable anti-wear and extreme-pressure performance by the use of chlorinated paraffins or waxes in their formulations. Very limited success has been realized in incorporating chlorinated derivatives in the newer synthetic fluids. This has been generally reported in *Lubrication Engineering*, vol. 37, pp. 715–721 (1981) and in *Journal of American Oil Chemists Society*, vol. 62, pp. 125–127 (1985). One example is the use of chlorinated fatty acids which are rendered water-soluble by salt formation with an amine or alkanolamine, such as triethanolamine. However, such ionic products interact with other additive components as well as with the calcium and magnesium ions usually present in a commercial water stream.

SUMMARY OF THE INVENTION

This invention relates to novel, improved additive compositions suitable for use in metalworking fluids. Such compositions comprise nonionic water-soluble polyoxyalkyl esters of chlorinated aliphatic carboxylic acids and aqueous systems, whether concentrated or dilute, including such fatty esters.

The compositions of this invention employ mono- and di-basic acids containing from 8 to about 36 carbon atoms which have been chlorinated to a level ranging from about 10 to about 50 wt. %. The compositions of this invention further employ a polymeric oxyalkyl grouping sufficiently large to impart substantially complete water solubility to the selected chloro-acid.

The additive compositions of this invention are particularly selected to impart improved anti-wear, lubricity and extreme-pressure properties when employed in synthetic metalworking fluids.

DESCRIPTION OF THE INVENTION

The novel compositions of this invention comprise water-soluble polyoxyalkyl esters of chlorinated aliphatic carboxylic acids as well as water-based metalworking fluids incorporating such fatty esters. These compositions afford a remarkable improvement over known salts of chlorinated acids, such as ethanolamine salts, both in anti-wear and extreme pressure properties and in stability relative to metal hardness factors in water, such as calcium and magnesium ions, and to other components of a metalworking fluid formulation.

Within the novel ester compositions of this invention, the acid moiety may be derived from any saturated aliphatic carboxylic acid having from about 8 to about 36 carbon atoms. For purposes of this invention, compositions derived from dimerized oleic or linoleic acid are considered as aliphatic derivatives. The acid moiety may also include dibasic as well as monobasic acids and may further include mixtures of either or both of these types.

The chlorinated acid precursors of the compositions of this invention may be prepared in any conventional procedure. For example, chlorine or hydrogen chloride may be added to doubly bonded carbon atoms of unsaturated acids. Chlorination of saturated acids may be employed. The resulting chloro acid should be a saturated molecule to avoid highly reactive centers as found in allylic halide derivatives. Chlorination of the selected aliphatic acid or acid mixture may proceed to a chlorine content varying from about 10 to about 50 wt. %, keeping in mind that the final additive composition of this invention should contain from about 4 to about 20 wt. % chlorine. A preferred chlorinated aliphatic carboxylic acid is trichlorostearic acid ($C_{17}H_{32}Cl_{13}COOH$), usually having one chlorine atom in the alpha position with the other two chlorine atoms randomly substituted. Another preferred chlorinated aliphatic carboxylic acid is a substantially equimolar mixture of trichlorostearic and trichloropalmitic acid ($C_{15}H_{28}Cl_3COOH$). Such a mixture is obtained in the chlorination of commercial stearic acid which affords such a mixture.

Within the novel ester compositions of this invention, the polyoxyalkyl moiety may include either or both of oxyethyl and oxypropyl groups. Esterification may be effected conventionally employing commercially available polyalkylene glycols. Optionally, the ester may be prepared by reaction of the selected acid with either ethylene oxide or propylene oxide. The polyoxyalkyl group provides the requisite water solubility and should be selected to be just sufficiently high in molecular weight to accomplish this. For example, when employing the preferred trichlorostearic acid adequate water solubility is achieved with from about 11 to 16 ethylene oxide units, so that the preferred monoester product has an average molecular weight within the range from about 800 to about 1000. Similarly, when employing a mixture of chlorinated stearic and palmitic acids, the average molecular weight will generally fall within the range from about 750 to about 1000.

When the additive compositions of this invention are prepared by esterification with a polyalkylene glycol, employing equimolar quantities of reactants, a minor portion of a diester product, as well as a similar molar portion of unreacted glycol, will be present. Any such chlorinated fatty acid diester has been found to perform similarly to the monoester but with a somewhat lesser solubility in water.

Where clarity of solution is not fully achieved, improved clarity may be achieved by including a small proportion (e.g., 2–3 wt. %) of free fatty acid in the ester product and additionally incorporating a small amount of an alkanolamine in the aqueous phase.

The additive compositions and derivative metalworking fluid concentrates of this invention, the latter typically containing from about 5 to about 15 wt. % of the additive composition, provide highly desirable extreme pressure and anti-wear performance, provide excellent lubricity and serve as highly desirable synthetic coolants. The metalworking fluids are preferably employed at dilution ratios of from about 4:1 to about 20:1 so that the additive composition is present in an amount from about 0.25 to about 3 wt. %.

The following examples are illustrative, without limitation, of the compositions of this invention.

EXAMPLE I

Commercial stearic acid was chlorinated under conventional conditions and a substantially trichlorostearic acid fraction was isolated. Esterification was effected by conventional reaction with a commercially available polyethylene glycol having an average molecular weight of about 600. The recovered ester product had the following properties.

| Appearance, 77° F. | Clear yellow liquid |
|---|---|
| Appearance, below 55° F. | Semisolid |
| Chlorine, % | 11 |
| Viscosity, SUS @ 100° F. | 830 |
| Viscosity, SUS @ 210° F. | 103 |
| Viscosity, cSt @ 40° C. | 162 |
| Viscosity, cSt @ 100° C. | 20 |
| Specific gravity @ 25° C. | 1.11 |
| Pounds per gallon @ 77° F. | 9.25 |
| Acid value | 3 |
| pH, 1% in water | 6.8 |

EXAMPLE II

The ester product of Example I was formulated to a heavy duty metalworking fluid having the following compositions.

| Ester product | 8.0 wt. % |
|---|---|
| Commercial polyglycol type lubricity agent | 8.0 |
| Commercial carboxylic salt type rust inhibitor | 3.0 |
| Commercial bactericide | 0.5 |
| Triethanolamine | 8.0 |
| Water | 72.5 |

The chlorine content of the formulated fluid was 0.88 wt. %.

EXAMPLE III

A commercial chlorinated fatty acid (28 wt. % chlorine) was formulated as in Example II. It was necessary to add 2.0 wt. % of a coupling agent (polyethylene glycol ester of tall oil fatty acids) to improve compatibility with other components of the formulation. The chlorine content of the formulated fluid was 2.24 wt. %.

EXAMPLE IV

The formulated metalworking fluids of Examples II and III were diluted 10:1 with water and evaluated employing the Falex Pin and Vee Block Tester, for measurement of lubricity and anti-wear. Falex procedures are described in *Lubrication Engineering*, vol. 24, pp. 349-358 (1968).

A simple Falex EP (extreme pressure) load and friction test was used. A cleaned steel #8 pin and blocks were placed in the machine and the reservoir was filled with test fluid. After a 1-minute break-in period at 250 pounds load, the ratchet arm was engaged and the load allowed to walk up to higher levels until failure. During walkup, torque was recorded at increments of 250 pounds. Torque is a measure of friction and boundary layer lubrication, with lower torque being desirable. The contribution of EP additives in the solution allows the test to proceed without seizure to higher loads before failure. Test results are presented in Table I, showing the superior performance of the fluid of Example II, even though a lower chlorine level was present as compared to the fluid of Example III. Failure occurred upon seizure, with snapping of the holding pins.

After completion of the Falex test, the pin finish from testing the fluid of Example II was visibly better than that from the test of the fluid of Example III.

EXAMPLE V

The ester product of Example I, formulated to a test fluid containing 20 wt. % ester, 10 wt. % triethanolamine, and 70 wt. % tap water, was held at 140° F. for 34 days to simulate extreme storage conditions. Its appearance remained clear. Base value decreased moderately from 40.2 to 33.1 due to hydrolysis of chlorine and resulting acid formation. The heat-stressed fluid was then diluted 20:1 with water and evaluated in Falex testing, as in Example IV. Comparison with a similar fluid, held at room temperature and suffering only negligible hydrolysis, showed no significant loss of effectiveness.

EXAMPLE VI

A neat sample of the ester product of Example I was maintained at 250° F. for 4 hours. There was no evolution of hydrogen chloride and no change from its original color of 8 Gardner.

TABLE I

| | Falex Tests | |
|---|---|---|
| | Torque, inch-lbs. | |
| Load, psi | Example II | Example III |
| 250 | 10 | 12 |
| 500 | 14 | 18 |
| 750 | 19 | 24 |
| 1000 | 23 | 28 |
| 1250 | 26 | 32 |
| 1500 | 28 | 37 |
| 1750 | 31 | 42 |
| 2000 | 34 | 47 |
| 2250 | 38 | 52 |
| 2500 | 40 | 55 |
| 2750 | 42 | 57 |
| 3000 | 44 | 58 |
| 3250 | 48 | 60 |
| 3500 | 50 | 62 |
| 3750 | Failed | Failed |

We claim:

1. An additive composition, comprising one or more water-soluble polyoxyalkyl esters of chlorinated aliphatic carboxylic acids, wherein:
   (a) the aliphatic carboxylic acids contain from about 8 to about 36 carbon atoms; and
   (b) the chlorine content of the chlorinated aliphatic carboxylic acids component is within the range from about 10 to about 50 wt. %.

2. The additive composition of claim 1, having a chlorine content within the range from about 4 to about 20 wt. %.

3. The additive composition of claim 1, wherein the aliphatic carboxylic acids are selected from the class consisting of monobasic acids, dibasic acids, and mixtures thereof.

4. The additive composition of claim 1, wherein the chlorinated aliphatic carboxylic acid component comprises substantially trichlorostearic acid.

5. The additive composition of claim 1, wherein the chlorinated aliphatic carboxylic acid component comprises a trichlorinated, substantially equimolar mixture of stearic and palmitic acids.

6. The additive composition of claim 1, wherein the polyoxyalkyl ester component is derived from the class consisting of polyoxyethyl groups, polyoxypropyl groups, and mixtures thereof.

7. The additive composition of claim 1, comprising polyoxyethyl esters of trichlorostearic acid having an average molecular weight within the range from about 800 to about 1000.

8. The additive composition of claim 1, comprising polyoxyethyl esters of a trichlorinated, substantially equimolar mixture of stearic and palmitic acids, having an average molecular weight within the range from about 750 to about 1000.

9. Water-based metalworking fluid concentrate comprising from about 5 to about 15 wt. % nonionic water-soluble polyoxyalkyl esters of chlorinated aliphatic carboxylic acids.

10. Metal-working fluid concentrates of claim 9, diluted further with water to provide from about 0.25 to about 3.0 wt. % nonionic water-soluble polyoxyalkyl esters of chlorinated aliphatic carboxylic acids.

* * * * *